United States Patent
Vellanki et al.

(10) Patent No.: US 8,703,980 B2
(45) Date of Patent: Apr. 22, 2014

(54) PROCESS FOR THE PREPARATION OF DARUNAVIR

(76) Inventors: Siva Rama Prasad Vellanki, Hyderabad (IN); Arabinda Sahu, Hyderabad (IN); Aravind Kumar Katukuri, Hyderabad (IN); Vikram Vanama, Hyderabad (IN); Satishbabu Kothari, Hyderabad (IN); Venkata Suryanarayana Ponnekanti, Hyderabad (IN); Debashish Datta, Hyderabad (IN)

( * ) Notice: Subject to any disclaimer, the term of this patent is extended or adjusted under 35 U.S.C. 154(b) by 21 days.

(21) Appl. No.: 13/496,642

(22) PCT Filed: Sep. 16, 2010

(86) PCT No.: PCT/IN2010/000625
§ 371 (c)(1),
(2), (4) Date: Jun. 21, 2012

(87) PCT Pub. No.: WO2011/048604
PCT Pub. Date: Apr. 28, 2011

(65) Prior Publication Data
US 2012/0251826 A1    Oct. 4, 2012

(30) Foreign Application Priority Data

| Sep. 17, 2009 | (IN) | 2257/CHE/2009 |
| Jan. 8, 2010 | (IN) | 54/CHE/2010 |
| Apr. 5, 2010 | (IN) | 939/CHE/2010 |

(51) Int. Cl.
C07D 493/04 (2006.01)
A61P 31/12 (2006.01)
A61P 31/18 (2006.01)

(52) U.S. Cl.
USPC .......................................... 549/464; 428/402

(58) Field of Classification Search
USPC .......................................... 549/464; 428/402
See application file for complete search history.

(56) References Cited

FOREIGN PATENT DOCUMENTS

WO    WO 2011017395 A1 *  2/2011

OTHER PUBLICATIONS

Tie, Y., High Resolution Crystal Structures of HIV-1 Protease with a Potent Non-Peptide Inhibitor (UIC-94017) Active Against Multdrug-resistant Clinical Strains, (2004) J. Mol. Biol.: 341-352.*
Surleraux, L.N.G., Discovery and Selection of TMC114, a Next Generation HIV-1 Protease Inhibitor,2005, J. Med. Chem. 48(6), 1813-1822.*

* cited by examiner

Primary Examiner — Andrew D Kosar
Assistant Examiner — John Mauro
(74) Attorney, Agent, or Firm — Ladas & Parry LLP

(57) ABSTRACT

A process for the preparation of Darunavir comprises the reacting of 4-amino-N-(2R, 3S) (3-amino-2-hydroxy-4-phenylbutyl)-N-isobutyl-benzenesulfonamide with (3R, 3aS, 6aR)-hexahydrofuro[2,3-b]furan-3-ol derivative in N-methyl-2-pyrrolidinone and isolating the resulting Darunavir. The process yields Darunavir with a very low level of the difuranyl impurity.

3 Claims, 1 Drawing Sheet

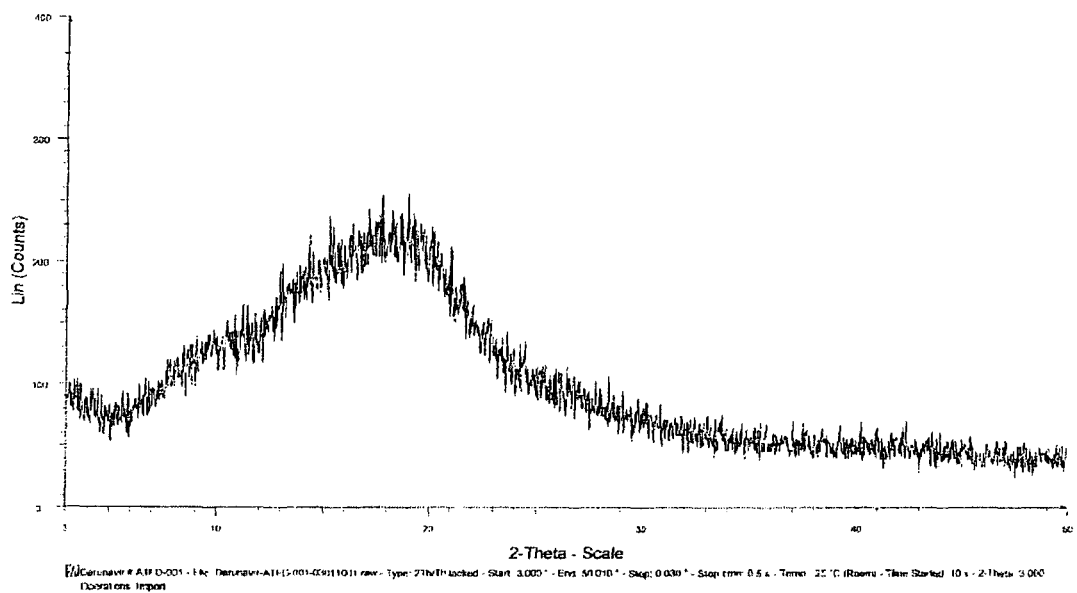
MATRIX LABORATORIES LTD

PROCESS FOR THE PREPARATION OF DARUNAVIR

This application claims priority to Indian patent application No. 2257/CHE/2009 filed on Sep. 17, 2009; 54/CHE/2010 filed on Jan. 8, 2010; and 939/CHE/2010 filed on Apr. 5, 2010, the contents of which are incorporated by reference in their entirety

FIELD OF THE INVENTION

The present invention relates to an improved process for the preparation of Darunavir, solvates or pharmaceutically acceptable salts.

The present invention also relates to Darunavir having substantially free of difuranyl impurity of formula (1).

Further, the present invention also relates to pharmaceutical composition of Darunavir, solvates or pharmaceutically acceptable salts having the difuranyl impurity of formula (1) less than 0.1%.

BACKGROUND OF THE INVENTION

Darunavir brand name is PREZISTA, formerly known as TMC114, which is used to treat HIV infection. It is a protease inhibitor developed by pharmaceutical company Tibotec. Darunavir is a second-generation protease inhibitor (PIs), designed specifically to overcome problems with the older agents in this class, such as indinavir.

Darunavir Ethanolate, has the chemical name: [(1S,2R)-3-[[(4-aminophenyl) sulfonyl](2-methylpropyl)amino]-2-hydroxy-1-(phenylmethyl)propyl]carbamic acid (3R,3aS,6aR)-hexahydrofuro[2,3-b]furan-3-yl ester monoethanolate and has the following structural formula:

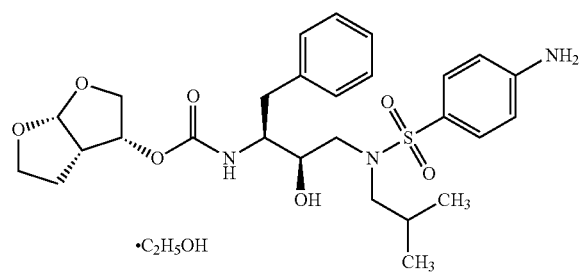 [SMILES: "·C2H5OH" ; CC(C)CN(C[C@@H](O)[C@H](Cc1ccccc1)NC(=O)O[C@H]1CO[C@H]2OCC[C@H]21)S(=O)(=O)c1ccc(N)cc1]

Darunavir and its process are first disclosed in U.S. Pat. No. 6,248,775, wherein 2R-hydroxy-3-[[(4-aminophenyl)sulfonyl](2-methylpropyl)amino]-1S(phenylmethyl) propylamine (4) is reacted with (3R,3aS,6aR)-hexahydrofuro[2,3-b]furan-3-ol in anhydrous acetonitrile in the presence of N,N'-disuccinimidyl carbonate, anhydrous pyridine at ambient temperature followed by workup to get Darunavir (Scheme A).

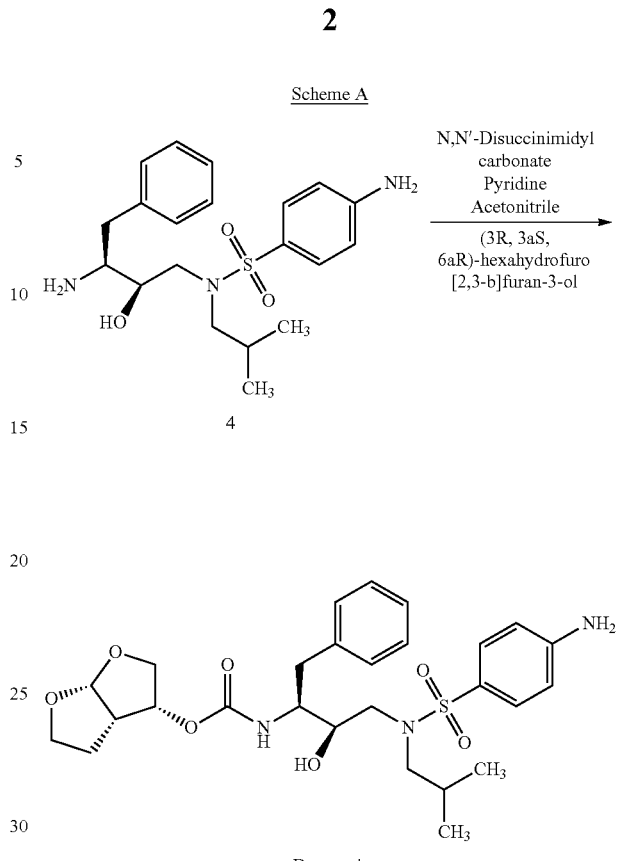

US 20050250845 disclosed the various solvates of Darunavir including ethanolate and method for their preparation as well as their use as a medicament. The same application disclosed the amorphous Darunavir by Raman spectra without process details.

WO 2005063770 discloses process for the preparation of Darunavir ethanolate, wherein 2R-hydroxy-3-[[(4-aminophenyl)sulfonyl](2-methylpropyl)amino]-1S-(phenylmethyl)propyl amine (4) is reacted with (3R,3aS,6aR)-hexahydrofuro[2,3-b]furan-3-ol in the presence of N,N'-disuccinimidyl carbonate, triethylamine, 41% methylamine in ethanol in a mixture of ethyl acetate and acetonitrile followed by workup and crystallization from ethanol to get Darunavir ethanolate (Scheme B).

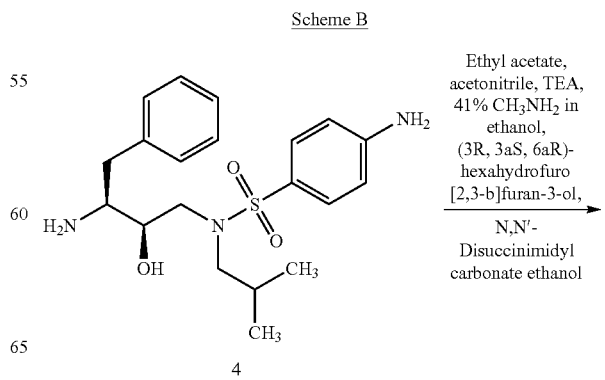

-continued

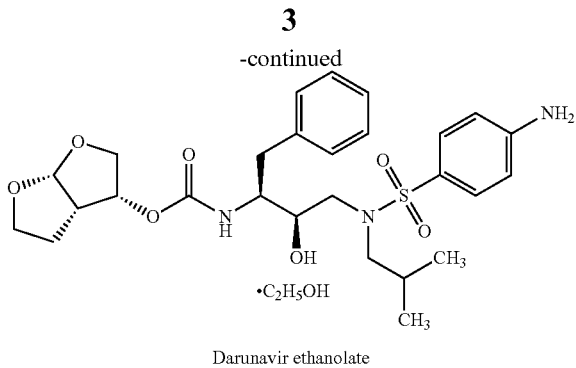

Darunavir ethanolate

In the prior art process, compound of formula 4 condensed with (3R,3aS,6aR)-hexahydrofuro[2,3-b]furan-3-ol in large excess of solvent or solvent mixture containing large excess of base or mixture of bases to get Darunavir. Further, the obtained products by the processes described in the prior art are not satisfactory, from purity point of view. We have repeated the Darunavir synthetic procedures as described in the prior art and found that relatively large amounts of impurities were obtained along with Darunavir (Table-1) which need repeated crystallizations in different solvents to get desired quality of the final product resulting in poor yields. Among other impurities, the carbonic acid [(1R,2S)-1-{((4-amino-benzenesulfonyl)-isobutyl-amino)-methyl}-2-((3R,3aS,6aR)-hexahydro-furo[2,3-b]furan-3-yloxycarbonylamino)-3-phenyl-propylester (3R,3aS,6aR)-hexahydro-furo[2,3-b]furan-3-yl ester (difuranyl impurity of formula 1) is identified.

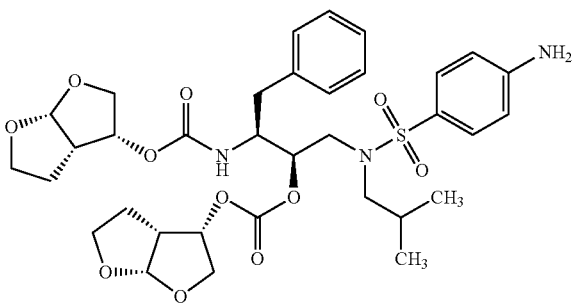

However, a need still remains for an improved and commercially viable process for preparing pure crystalline or amorphous Darunavir that should solve the aforesaid problems associated with processes described in the prior art, which will be suitable for large-scale preparation, in terms of simplicity, yield and purity of the product. The inventors of the present invention also developed a novel process for amorphous Darunavir, which is feasible at large scale.

SUMMARY AND OBJECT OF THE INVENTION

The main aspect, the present invention is to provides an improved process for the preparation of Darunavir, solvates or its pharmaceutically acceptable salts having substantially free of difuranyl impurity.

In another aspect, the present invention provides Darunavir, solvates or its pharmaceutically acceptable salts having difuranyl impurity is less than 0.1%.

In another aspect, the present invention provides process for the preparation of Darunavir which comprises, a) reacting 4-amino-N-(2R,3S) (3-amino-2-hydroxy-4-phenylbutyl)-N-isobutyl-benzenesulfonamide (4) with (3R,3aS,6aR)-hexahydrofuro[2,3-b]furan-3-ol derivative (5) in N-methyl-2-pyrrolidinone (NMPO) solvent, and
b) isolating Darunavir.

In another aspect, the present invention provides amorphous Darunavir, having particle size $D_{50}$ is less than 60 micrometers and $D_{90}$ less than 200 micrometers.

In another aspect, the present invention provides Darunavir, having the purity more than 99.5% and difuranyl impurity less than 0.10%.

In another aspect, the present invention provides an improved process for the preparation of amorphous Darunavir comprising the steps of:
a) dissolving Darunavir or Darunavir solvate in an organic solvent, and
b) removing the solvent to obtain amorphous form of Darunavir.

In another aspect, the present invention provides an improved process for the preparation of amorphous Darunavir comprising the steps of;
a) dissolving Darunavir in an organic solvent,
b) removing the solvent,
c) adding hydrocarbon solvent, and
d) isolating amorphous form of Darunavir.

In another aspect, the present invention provides a process for preparation of amorphous Darunavir by forming a melt by heating the Darunavir followed by fast cooling the melt to form amorphous Darunavir.

In another aspect, the present invention provides a process for the preparation of amorphous Darunavir comprising the steps of;
a) suspending Darunavir in an organic solvent,
b) adding an anti-solvent, and
c) isolating amorphous Darunavir.

In yet another aspect, the present invention provides a process for preparation of amorphous Darunavir, which comprises:
a) providing a solution, suspension or dispersion of Darunavir or Darunavir solvate, either alone or in combination with one or more pharmaceutically acceptable carriers, in a solvent; and
b) removing solvent from the solution to provide the desired amorphous Darunavir.

In yet another aspect, the present invention provides a pharmaceutical composition comprising Darunavir or solvate or pharmaceutically acceptable salt and at least one pharmaceutically acceptable carrier

BRIEF DESCRIPTION OF THE FIGURES

FIG. 1 is a representative X-ray diffraction pattern of amorphous form of Darunavir

DETAILED DESCRIPTION OF THE INVENTION

The present invention relates to an improved process for the preparation of Darunavir, solvates or pharmaceutically acceptable salt, substantially free of difuranyl impurity of formula (1).

The term "crushed" used in the present invention may be understood as grinding, breaking, pressing or compressing.

The term "suspending" used in the present invention may be understood as slurrying, partial dissolving, dissolving, contacting or treating.

The term "substantially" used in the present invention is Darunavir having difuranyl impurity is less than 0.2%, preferably less than 0.1%, more preferably less than 0.05%.

In one embodiment, amorphous Darunavir having the difuranyl impurity less than 0.1% is prepared by the process comprising the steps of:

a) reacting isobutylamine with protected (2S,3S)-1,2-epoxy-3-amino-4-phenylbutane (2), followed by with p-nitrobenzenesulfonyl chloride in a solvent in the presence of a base to obtain corresponding protected N-((2R,3S)-3-amino-2-hydroxy-4-phenylbutyl)-N-isobutyl-4-nitro-benzenesulfonamide (3),

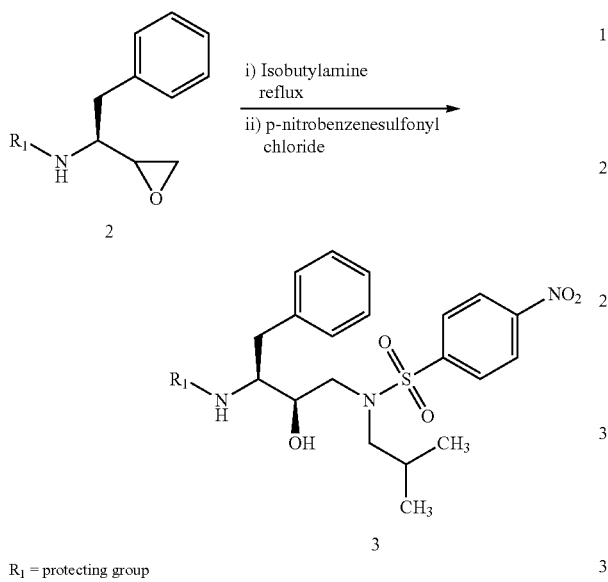

b) reducing the compound of formula 3, followed by hydrolyzing to obtain a compound of formula 4,

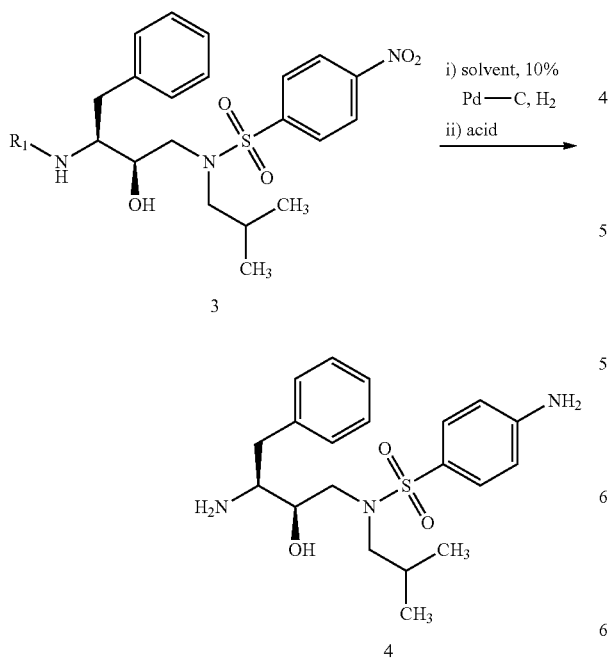

c) coupling the compound of formula 4 with (3R,3aS,6aR)-hexahydrofuro[2,3-b]furan-3-ol derivative (5) in a solvent to obtain Darunavir,

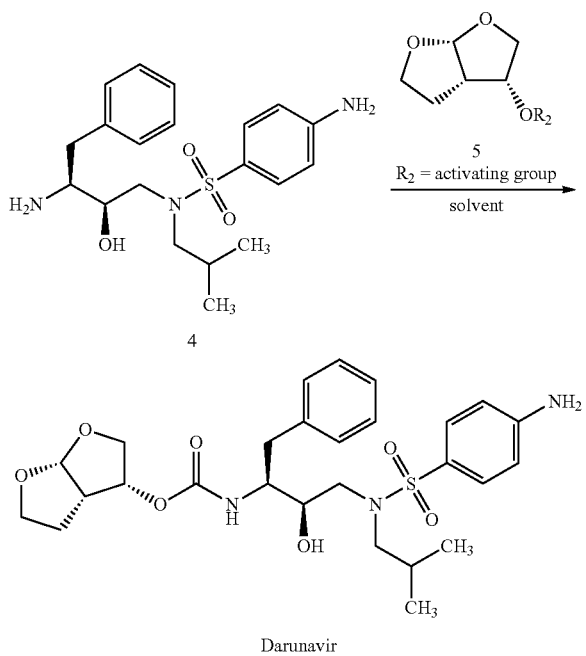

d) optionally converting the Darunavir to Darunavir solvate,

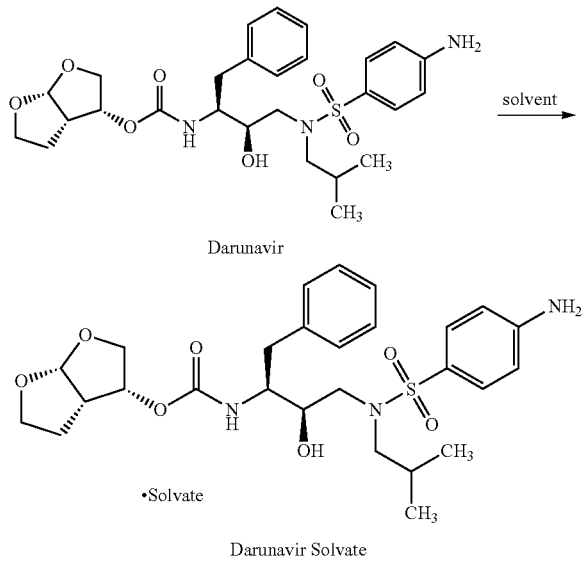

e) dissolving the Darunavir or Darunavir solvate in a solvent, and f) isolating the amorphous Darunavir.

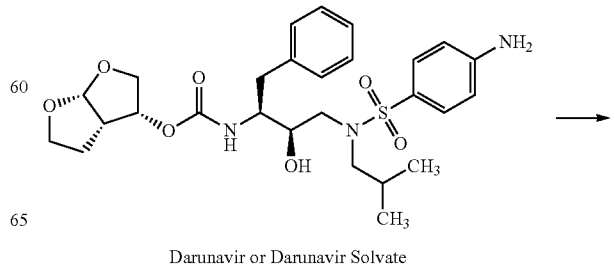

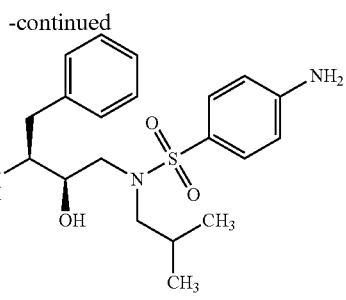

Amorphous Darunavir

According to the present invention, compound of formula 2 is reacted with isobutylamine under reflux temperature and then excess isobutylamine is removed under reduced pressure. The obtained residue is dissolved in a solvent and reacted with p-nitrobenzenesulfonyl chloride in the presence of a base at reflux temperature. The compound of formula 3 is isolated by filtration and further subjected to recrystallisation to obtain pure compound of formula 3.

The solvent used in step a) is selected from methylene dichloride, chloroform, N,N-dimethylformamide, dimethyl sulfoxide, N-methyl-2-pyrrolidinone, ethyl acetate, dimethylacetamide or mixture thereof.

The base used in step a) is selected from alkyl amines like ammonia, methylamine, ethylamine, dimethylamine, diethylamine, triethylamine, N,N-diisopropylethylamine and aromatic amines like, N,N-dimethylaniline, N,N-dimethylaminopyridine or mixture thereof.

The solvent used for recrystallisation of compound 3 is selected from the methanol, ethanol, isopropyl alcohol, ethyl acetate, isopropyl acetate or mixture thereof.

The protecting group in step a) is selected from t-butoxycarbonyl (Boc), benzyloxycarbonyl (Cbz), trityl (Trt), 9-fluoroenylmethoxycarbonyl (Fmoc), 2-(4-biphenylyl)propyl(2) oxycarbonyl (Bpoc), 2-phenylpropyl(2)oxycarbonyl (Poc), 2-(4-xenyl)isopropoxycarbonyl, isopropoxycarbonyl, 1,1-diphenylethyl(I)oxycarbonyl, 1,1-diphenylpropyl(1)oxycarbonyl, 2-(3,5-dimethoxyphenyl)-propyl(2)-oxycarbonyl (Ddz), 2-(p-5-toluoyl)propyl(2)oxycarbonyl, 1-methylcyclopentanyloxycarbonyl, cyclohcxanyloxycarbonyl, 1-methyl-cyclohcxanyloxocarbonyl, 2-methylcyclohexanyloxycarbonyl, ethoxycarbonyl, 2-(4-toluoylsulfonyl)ethoxycarbonyl, 2-(methylsulfonyl)ethoxycarbonyl, 2-(triphenyl-phosphino) ethoxycarbonyl, 2-(trimethylsilyl)ethoxycarbonyl, allyloxycarbonyl, 1-prop-1-enyloxycarbonyl, 5-benzisoxalylmethoxycarbonyl, 4-acetoxybenzyloxycarbonyl, 2,2,2-trichloroethoxycarbonyl, tribromoethoxycarbonyl, 2-ethyl (2)propoxycarbonyl, cyclopropylmethoxycarbonyl, isobornyloxycarbonyl, 1-piperidyloxycarbonyl, 4-phenylbenzyloxycarbonyl, 2-methylbenzyloxycarbonyl, α-2,4,5,-tetramethylbenzyloxycarbonyl (Tmz), 4-methoxybenzyloxycarbonyl, 4-fluorobenzyloxycarbonyl, 4-chlorobenzyl oxycarbonyl, 3-chlorobenzyloxycarbonyl, 2-chlorobenzyloxycarbonyl, dichlorobenzyloxycarbonyl, 4-bromo-benzyloxycarbonyl, ortho-bromobenzyloxycarbonyl, 3-bromobenzyloxycarbonyl, 4-nitrobenzyloxycarbonyl, 4-cyanobenzyloxycarbonyl, 4-(decyloxy)-benzyloxycarbonyl, and the like; the benzoylmethylsulfonyl group, dithiasuccionyl (Dts) group, the 2-(nitro)phenylsulfenyl group (Nps), the diphenylphosphine oxide group.

According to the present invention, the reduction is carried out by dissolving the compound of formula 3 in a solvent, optionally containing triethanolamine and reducing with metallic reducing reagents, optionally, under hydrogen atmosphere. The obtained product is subjected to hydrolysis with an acid in same solvent followed by recrystallisation to isolate a compound of formula 4.

The compound of formula 3 is dissolved in a solvent selected from methanol, ethanol, isopropyl alcohol, ethyl acetate or mixture thereof. The reduction was carried out at the temperature in the range of 30-55° C.

The reducing agent suitable for reduction of the nitro moiety is selected from borane complexes such as diborane, sodium borohydride, lithium borohydride, sodium borohydride-LiCl, aluminum lithium hydride, or diisobutylaluminium hydride; metals such as iron, zinc, tin and the like; and transition metals such as palladium-carbon, platinum oxide, Raney-nickel, rhodium, ruthenium and the like. When catalytic reduction is applied, ammonium formate, sodium dihydrogenphosphate, hydrazine may be used as the hydrogen source.

The reagent for the hydrolysis is selected from inorganic acids such as hydrochloric acid, nitric acid, sulfuric acid and phosphoric acid; organic acids such as acetic acid, trifluoroacetic acid methanesulfonic acid and p-toluenesulfonic acid; Lewis acids such as boron trifluoride; acidic cationic ion-exchange resins such as Dowex SOWTM.

The solvent used for the recrystallisation of compound of formula 4 is selected from methanol, ethanol, isopropyl alcohol, ethyl acetate or mixture thereof.

According to the present invention, a solution of compound of formula 4 in an organic solvent is added slowly to a solution of compound of formula 5 in same organic solvent at −5° C. to 5° C. and maintained at ambient temperature for 4-10 h. to get crude Darunavir. The obtained crude Darunavir is optionally converted to its solvate followed by recrystallisation in a solvent. The Darunavir solvate is further converted to amorphous Darunavir by dissolving in an organic solvent and evaporating the solvent by using known techniques.

The compound of formula 5 is generated by activating (3R,3aS,6aR)-hexahydrofuro[2,3-b]furan-3-ol (5a) with coupling agents which may undergo carbamoylation with compound of formula 4. The compound of formula 5a is activated with the coupling agent preferably occurs before the coupling with compound of formula 4 and is additional advantage to be a one-pot procedure, since isolation of the activated intermediate is not necessary. Examples of coupling agents used in carbamoylation reactions are carbonates such as bis-(4-nitrophenyl)carbonate, disuccinimidyl carbonate (DSC), carbonyl diimidazole (CDI). Other coupling agents include chloroformates, such as p-nitrophenylchloroformate, phosgenes such as phosgene or triphosgene.

The solvent used in the step d) to prepare a solution of compound of formula 4 is selected from N-methyl-2-pyrrolidinone (NMPO), N,N-dimethylformamide, ethyl acetate, tetrahydrofuran, acetonitrile, dioxane, methylene dichloride or mixture thereof.

The solvent used to prepare Darunavir solvate is selected from methanol, ethanol, isopropyl alcohol, n-propanol, n-butanol, ethyl acetate, tetrahydrofuran, methyl ethyl ketone, methyl t-butyl ether, diisopropyl ether or mixtures thereof.

The solvent used for recrystallisation Darunavir solvate is selected from methanol, ethanol, isopropyl alcohol, n-propanol, n-butanol, ethyl acetate, tetrahydrofuran, methyl ethyl ketone, methyl t-butyl ether, diisopropyl ether or mixtures thereof.

The organic solvent used to dissolve Darunavir or Darunavir solvate to prepare amorphous Darunavir is selected from dichloromethane, chloroform, carbon tetrachloride, dichloroethane, tetrahydrofuran, ethyl acetate or mixture thereof. The technique to evaporate the solvent is selected from distillation, evaporation, spray drying, freeze drying, lyophilisation or agitated thin film drier (ATFD).

The reactions involved in the present invention are depicted Scheme C:

Scheme C

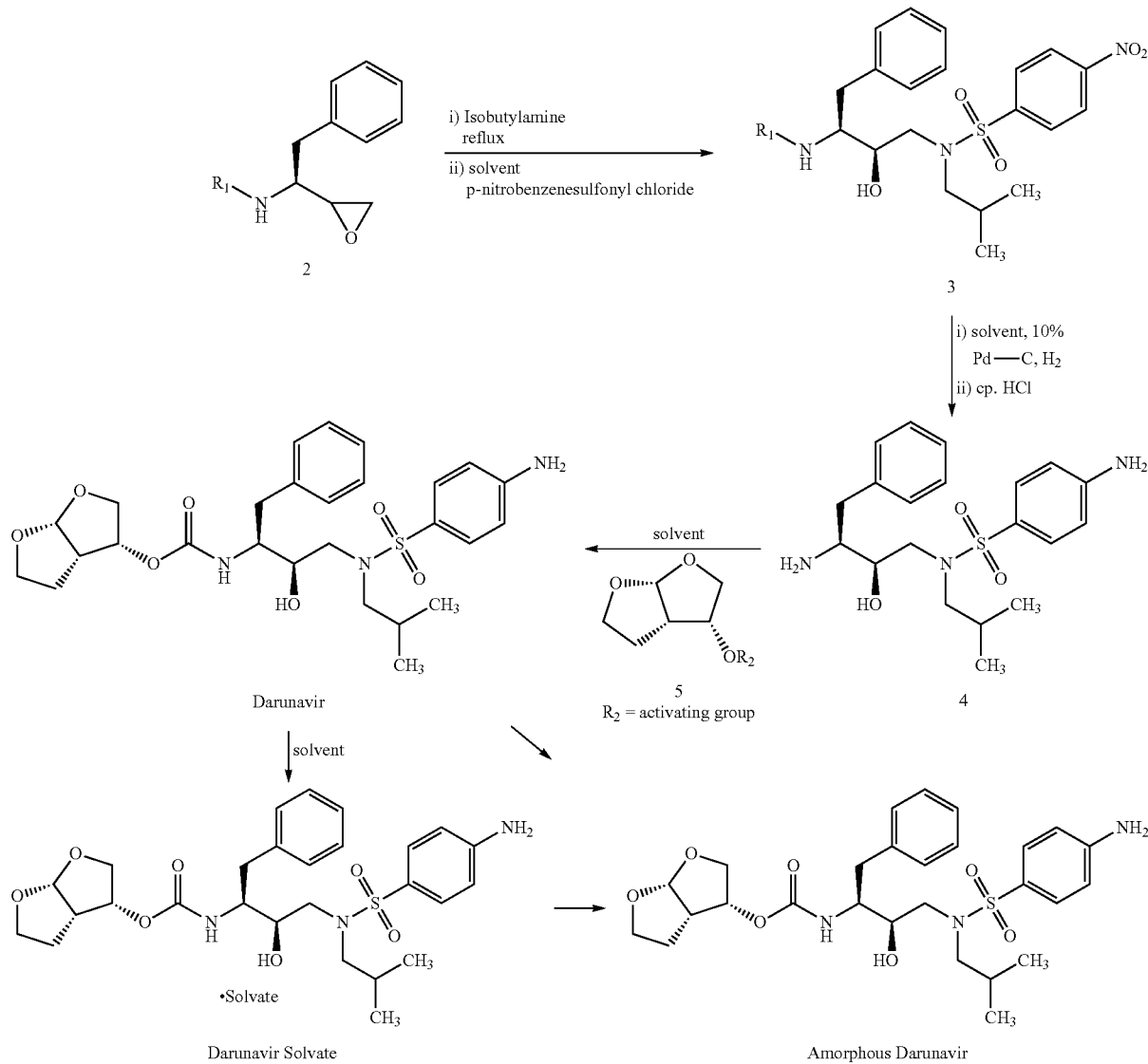

R₁ = protecting group

In another embodiment, amorphous Darunavir having the difuranyl impurity of formula (1) less than 0.1% is prepared by the process comprising the steps of:

a) reacting compound of formula 6 with isobutylamine in presence of base to obtain compound of formula 7,

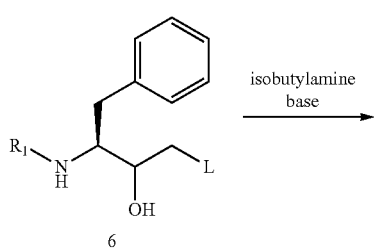

isobutylamine
base

R₁ = protecting group
L = leaving group

-continued

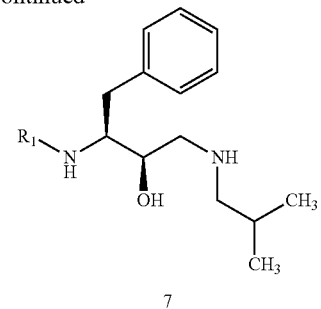

b) reacting the compound of formula 7 with p-nitrobenzenesulfonyl chloride in an organic solvent in the presence of a base to obtain corresponding protected N-((2R,3S)-3-amino-2-hydroxy-4-phenylbutyl)-N-isobutyl-4-nitrobenzenesulfonamide (3),

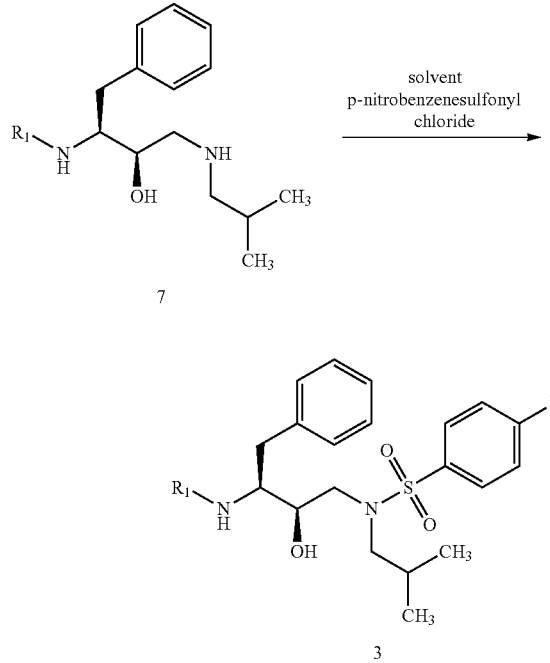

R₁ = protecting group c) reducing the compound of formula 3 to obtain a compound of formula 4,

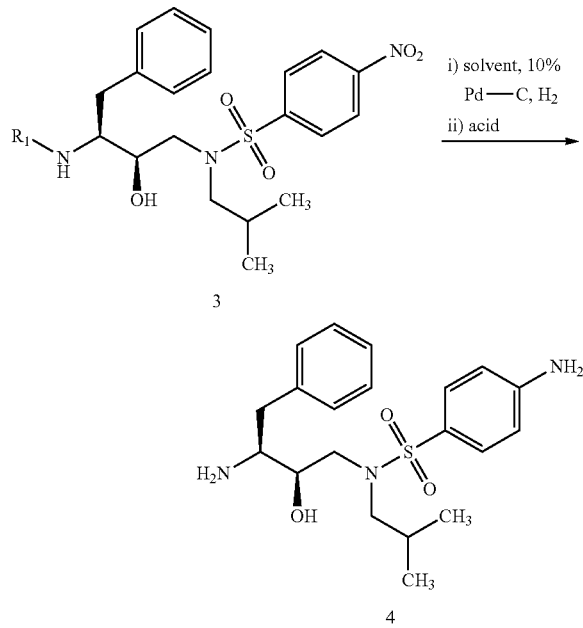

d) coupling the compound of formula 4 with (3R,3aS,6aR)-hexahydrofuro[2,3-b]furan-3-ol derivative (5) in a solvent to obtain Darunavir,

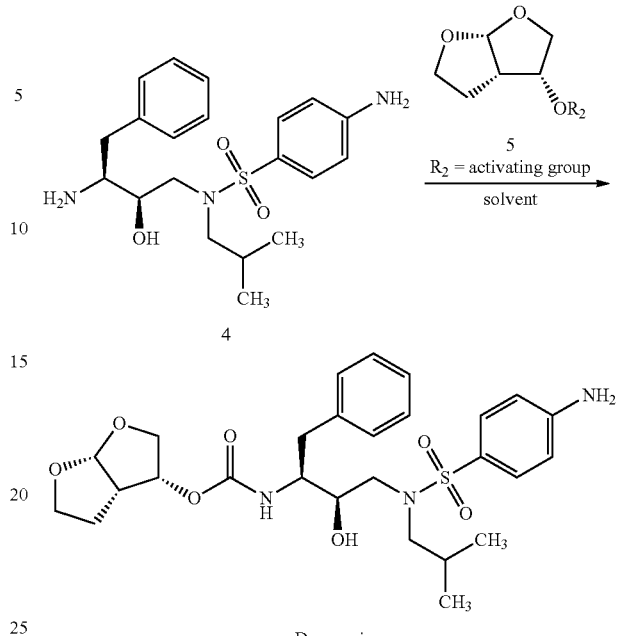

e) optionally converting the Darunavir to Darunavir solvate,

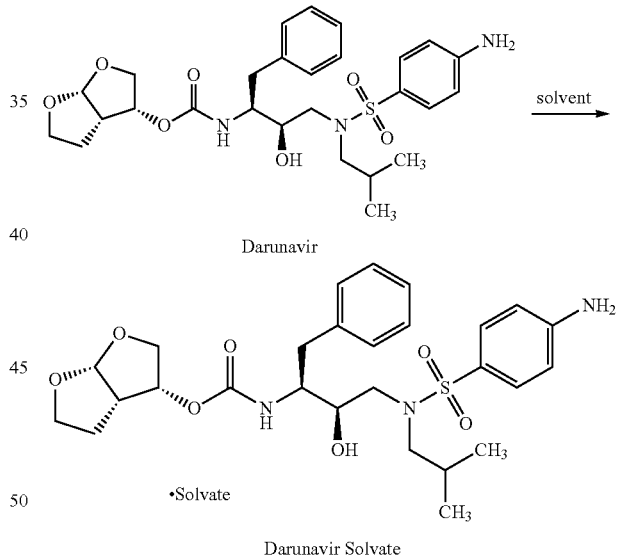

f) dissolving the Darunavir or Darunavir solvate in a solvent, and
g) isolating the amorphous Darunavir.

According to the present invention, compound of formula 6 is reacted with isobutylamine in a solvent or mixture thereof in the presence of base at reflux temperature and then excess isobutylamine is removed under reduced pressure to obtain compound of formula 7.

The solvent used in the step a) is selected from water, methylenedichloride, methanol, ethanol, 3-propanol, n-butanol, 2-butanol, ethyl acetate, isopropyl acetate, toluene, N,N-dimethylformamide, N,N-dimethylacetamide, N-methyl-2-pyrrolidinone (NMPO), dimethyl sulfoxide or mixture thereof.

The base used in the step a) is selected from sodium hydroxide, potassium hydroxide, lithium hydroxide, sodium carbonate, potassium carbonate, lithium carbonate, sodium bicarbonate, potassium bicarbonate or lithium bicarbonate.

The leaving group in the present invention is selected from chloro, bromo, iodo or cyano.

The obtained compound of formula 7 is reacted with p-nitrobenzenesulfonyl chloride in an organic solvent in the presence of a base at reflux temperature to obtain compound of formula 3. Further, the compound of formula 3 is subjected to recrystallisation to obtain pure product.

The solvent used in step b) is selected from methylene dichloride, toluene, N,N-dimethylformamide, dimethyl sulfoxide, N-methyl-2 pyrrolidinone, ethyl acetate, dimethylacetamide or mixture thereof.

The base used in step b) is selected from alkyl amines like ammonia, methylamine, ethylamine, dimethylamine, diethylamine, triethylamine, N,N-diisopropylethylamine and aromatic amines like, N,N-dimethylaniline, N,N-dimethylaminopyridine or mixture thereof.

The solvent used to recrystallisation the compound of step b) is selected from the methanol, ethanol, isopropyl alcohol, ethyl acetate, isopropyl acetate or mixture thereof.

According to the present invention, the reduction is carried out by dissolving the compound of formula 3 in a solvent, optionally containing triethanolamine and reducing with metallic reducing reagents, optionally, under hydrogen atmosphere. The obtained product is subjected to hydrolysis with an acid in same solvent followed by recrystallisation to isolate a compound of formula 4.

The compound of formula 3 is dissolved in a solvent selected from methanol, ethanol, isopropyl alcohol, ethyl acetate or mixture thereof. The reduction was carried out at the temperature in the range of 30-55° C.

The reducing agent suitable for reduction of the nitro moiety is selected from borane complexes such as diborane, sodium borohydride, lithium borohydride, sodium borohydride-LiCl, aluminum lithium hydride, or diisobutylaluminium hydride; metals such as iron, zinc, tin and the like; and transition metals such as palladium-carbon, platinum oxide, Raney-nickel, rhodium, ruthenium and the like. When catalytic reduction is applied, ammonium formate, sodium dihydrogenphosphate, hydrazine may be used as the hydrogen source.

The reagent for the hydrolysis is selected from inorganic acids such as hydrochloric acid (commercially pure or laboratory grade), nitric acid, sulfuric acid and phosphoric acid; organic acids such as acetic acid, trifluoroacetic acid methanesulfonic acid and p-toluenesulfonic acid; Lewis acids such as boron trifluoride; acidic cationic ion-exchange resins such as Dowex SOWTM.

The solvent used for the recrystallisation of compound of formula 4 is selected from methanol, ethanol, isopropyl alcohol, ethyl acetate or mixture thereof.

According to the present invention, a solution of compound of formula 4 in an organic solvent is condensed with a solution of compound of formula 5 in an organic solvent at −10° C. to 40° C. and maintained at ambient temperature for 4-10 h. to get crude Darunavir. The obtained crude Darunavir is optionally converted to its solvate followed by recrystallisation from an organic solvent. The Darunavir solvate is further converted to amorphous Darunavir by dissolving in an organic solvent and evaporating the solvent by using known techniques.

The compound of formula 5 is generated by activating (3R,3aS,6aR)-hexahydrofuro[2,3-b]furan-3-ol (5a) with coupling agents which may undergo carbamoylation with compound of formula 4. The compound of formula 5a is activated with the coupling agent preferably occurs before the coupling with compound of formula 4 and is additional advantage to be a one-pot procedure, since isolation of the activated intermediate is not necessary. Examples of coupling agents used in carbamoylation reactions are carbonates such as bis-(4-nitrophenyl)carbonate, disuccinimidyl carbonate (DSC), carbonyl diimidazole (CDI). Other coupling agents include chloroformates, such as p-nitrophenylchloroformate, phosgenes such as phosgene or triphosgene.

The solvent used in the step e) and to prepare a solution of compound of formula 4 is selected from N-methyl-2-pyrrolidinone (NMPO), N,N-dimethylformamide, ethyl acetate, tetrahydrofuran, acetonitrile, dioxane, methylene dichloride or mixture thereof.

The solvent used to prepare Darunavir solvate is selected from methanol, ethanol, isopropyl alcohol, n-propanol, n-butanol, ethyl acetate, tetrahydrofuran, methyl ethyl ketone, methyl t-butyl ether, diisopropyl ether or mixtures thereof.

The solvent used for recrystallisation Darunavir solvate is selected from methanol, ethanol, isopropyl alcohol, n-propanol, n-butanol, ethyl acetate, tetrahydrofuran, methyl ethyl ketone, methyl t-butyl ether, diisopropyl ether or mixtures thereof.

The organic solvent used to dissolve Darunavir or Darunavir solvate to prepare amorphous Darunavir is selected from dichloromethane, chloroform, carbon tetrachloride, dichloroethane, tetrahydrofuran, ethyl acetate or mixture thereof. The technique to evaporate the solvent is selected from distillation, evaporation, spray drying, freeze drying, lyophilisation or agitated thin film drier (ATFD).

In another embodiment, the present invention provide a process for the preparation of the Darunavir having the difuranyl impurity of formula (I) less than 0.1% is prepared by coupling the compound of formula 4 with (3R,3aS,6aR)-hexahydrofuro[2,3-b]furan-3-ol derivative (5) in N-methyl-2-pyrrolidinone (NMPO).

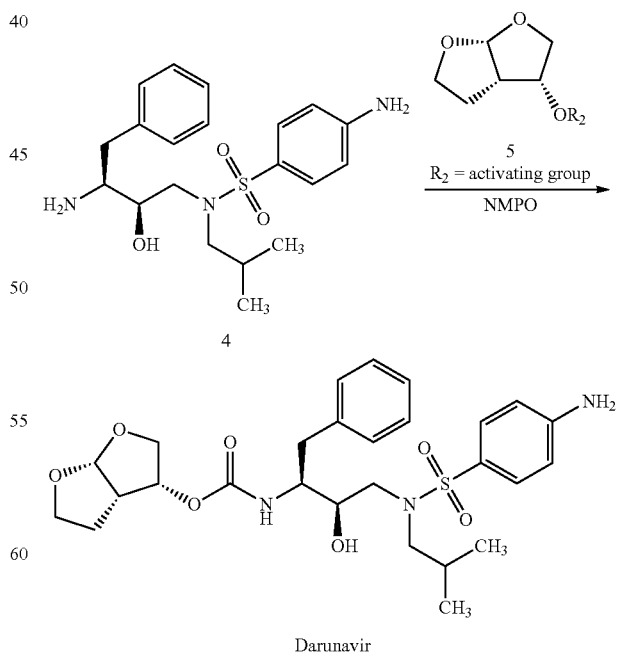

Darunavir

According to the present invention, a solution of compound of formula 4 in an organic solvent is added slowly to a solution of compound of formula 5 in same organic solvent at −5° C. to 5° C. and maintained at ambient temperature for 4-10 h. to get Darunavir.

The compound of formula 5 is generated by activating (3R,3aS,6aR)-hexahydrofuro[2,3-b]furan-3-ol (5a) with coupling agents which may undergo carbamoylation with compound of formula 4. The compound of formula 5a is activated with the coupling agent preferably occurs before the coupling with compound of formula 4 and is additional advantage to be a one-pot procedure, since isolation of the activated intermediate is not necessary. Examples of coupling agents used in carbamoylation reactions are carbonates such as bis-(4-nitrophenyl)carbonate, disuccinimidyl carbonate (DSC), carbonyl diimidazole (CDI). Other coupling agents include chloroformates, such as p-nitrophenylchloroformate, phosgenes such as phosgene or triphosgene.

In another embodiment, the present invention provides a process for the preparation of amorphous Darunavir comprising the steps of:
 a) dissolving Darunavir in a solvent, and
 b) isolating amorphous Darunavir.

According to the present invention, Darunavir is dissolved in a solvent such as dichloromethane, chloroform, carbon tetrachloride, dichloroethane, tetrahydrofuran, methanol, ethanol, isopropyl alcohol, acetonitrile, ethyl acetate or mixtures thereof and then solvent is removed by conventional techniques such as distillation, evaporation, spray drying, freeze drying, lyophilisation or agitated thin film drier (ATFD) and thus isolating amorphous Darunavir.

In another embodiment, the present invention provides a process for the preparation of amorphous Darunavir comprising the steps of:
 a) dissolving Darunavir in a solvent,
 b) removing the solvent,
 c) adding hydrocarbon solvent, and
 d) isolating amorphous Darunavir.

According to the present invention, Darunavir is dissolved in a solvent such as ethyl acetate, isopropyl acetate, methyl acetate, acetone or tetrahydrofuran, then heated the solution to 35-50° C. and maintained at the same temperature for about 1 h. The solvent is removed by distillation, followed by addition of hydrocarbon solvent selected from n-hexane, n-heptane, cyclohexane, diethyl ether, petroleum ether, methyl tert-butyl ether, octane or toluene and the obtain solid is filtered to get amorphous form of Darunavir.

In another embodiment, the present invention provides a process for preparation of amorphous Darunavir comprising the steps of:
 a) heating the Darunavir to higher temperature to form melt,
 b) cooling the melt, and
 c) isolating the amorphous Darunavir.

According to the present invention, Darunavir is heated to 110-120° C. to form a melt and maintained the melt for 3-5 h. at the same temperature under vacuum. The melt was cooled to 25-35° C. to form glass type crystals. The obtained glass type crystals were crushed to obtain amorphous Darunavir.

In another embodiment, the present invention provides a process for the preparation of amorphous Darunavir comprising the steps of:
 a) suspending Darunavir in a solvent,
 b) heating the reaction mass to higher temperatures,
 c) cooling the reaction mass,
 d) adding an anti-solvent, and
 e) isolating amorphous Darunavir.

According to the present invention, Darunavir is suspended in a solvent such as glycerol then heated to 80-130° C. preferably 80-120° C. and maintained under vacuum for about 1 hr. The resultant solution was cooled to an ambient temperature and added anti-solvent selected from water, n-hexane, n-heptane, cyclohexane, diethyl ether, petroleum ether, methyl tert-butyl ether, octane or toluene and the obtained solide is filtered to get amorphous Darunavir.

According to the present invention Darunavir used as input in the above processes may be in the form of hydrate, anhydrous or solvate such as ethanol solvate, methanol solvate, isopropanol solvate, acetone solvate or solvated hydrate.

In another embodiment, the present invention provides Darunavir ethanolate obtained from the present process have the purity more than 99.5% and difuranyl impurity is less than 0.08%.

In another embodiment, the present invention provides amorphous Darunavir obtained from the present process have the purity more than 99.5% and difuranyl impurity is less than 0.08%.

In another embodiment, the present invention provides amorphous Darunavir, having particle size $D_{50}$ is less than 60 micrometers and $D_{90}$ less than 200 micrometers.

In another embodiment, the present invention provides pharmaceutical composition of Darunavir, solvates or its pharmaceutically acceptable salts having difuranyl impurity is less than 0.1%.

In another embodiment, the present invention provides a process for preparation of amorphous Darunavir, which comprises:
 a) providing a solution, suspension or dispersion of Darunavir or Darunavir solvate, either alone or in combination with one or more pharmaceutically acceptable carriers, in a solvent; and
 b) removing solvent from the solution to provide the desired amorphous Darunavir.

According to the present invention Darunavir is dissolved in a solvent, pharmaceutically acceptable carrier like povidone is added and removed the solvent by distillation, filtration, freeze drying of azitated thin film drier.

In another embodiment, the present invention provides a pharmaceutical composition comprising Darunavir or solvate or pharmaceutically acceptable salt and at least one pharmaceutically acceptable carrier.

According to the present invention, Darunavir was prepared by the processes given in the prior art and the results are provided in Table 1. The obtained product is of low quality and poor yield.

TABLE 1

| Solvent | Complex (mode of addition) | Base | Temp. addition | Temp. maintain | difuranyl Imp. |
|---|---|---|---|---|---|
| Acetonitrile | Single lot | TEA | 25° C. | 25-30° C. | 0.58% |
| Acetonitrile | Single lot | TEA | 25° C. | 40-45° C. | 1.07% |
| Acetonitrile | Single lot | TEA | 25° C. | 70-75° C. | 1.16% |
| Acetonitrile | 60 min. | TEA | 25° C. | 25-30° C. | 0.64% |
| Acetonitrile | 120 min. | TEA | 25-30° C. | 25-30° C. | 0.41% |
| Acetonitrile | 120 min. | TEA | 25-30° C. | 40-45° C. | 0.92% |
| Acetonitrile | 90 min. | TEA | 40-45° C. | 40-45° C. | 0.52% |
| Acetonitrile | 180 min. | — | 0-5° C. | 25-30° C. | 0.88% |
| Toluene | 60 min. | TEA | 0-5° C. | 25-30° C. | 0.98% |

The experimental results of the present invention are given in Table 2.

TABLE 2

| Solvent | Complex (mode of addition) | Base | Temp. addition | Temp. maintain | difuranyl Imp. |
|---|---|---|---|---|---|
| THF | 60 min. | 4-DMAP | 25-30° C. | 25-30° C. | 0.88% |
| DMF | 120 min. | — | −4 to 0° C. | 25-30° C. | 0.10% |
| NMPO | 60 min. | 4-DMAP | 25-30° C. | 25-30° C. | 0.08% |
| NMPO | 90 min. | — | −4 to 0° C. | 25-30° C. | 0.08% |
| NMPO | 120 min. | — | −4 to 0° C. | 25-30° C. | 0.07% |
| NMPO | 150 min. | — | −4 to 0° C. | 25-30° C. | 0.06% |
| NMPO | 150 min. | — | −10 to 7° C. | 25-30° C. | 0.07% |

Compositions comprising the Darunavir prepared as per the present invention can be made by conventional methods, for instance, compression or granulation of above Darunavir with pharmaceutically acceptable excipients. The composition can be in the form of tablets, capsules, caplets etc.

Darunavir prepared by the present process has overcome the difficulties in the prior art and has the following advantages:
a) process is simple to operate;
b) process results in improved yield and quality;
c) process results in Darunavir with difuranyl impurity in less than 0.1% by HPLC.

The following examples are provided for illustrative purposes only and are not intended to limit the scope of the invention in any way.

EXPERIMENTAL SECTION

Powder X-ray Diffraction (PXRD)

The X-ray diffraction patterns of said polymorphs of the invention were measured on Bruker D8 Discover powder diffractometer equipped with goniometer of θ/θ configuration and LynxEye detector. The Cu-anode X-ray tube was operated at 40 kV and 30 mA. The experiments were conducted over the 2θ range of 2.0°-50.0°, 0.030° step size and 50 seconds step time.

Example-1

Preparation of (1S,2R)-{1-benzyl-2-hydroxy-3-[isobutyl-(4-nitrobenzene sulfonyl)-amino]propyl}-carbamic acid tert-butyl ester (3a)

Method A

A solution of (2S,3S)-1,2-epoxy-3-(butoxycarbonyl) amino-4-phenylbutane (2a, 100 g, 0.380 mol) of) in isobutylamine (150 g, 2.05 mol) of) was heated under and maintained for 3 h. After completion of the reaction, excess of isobutylamine was removed under reduced pressure. Isobutylamine traces were removed by flushing with methylene dichloride. The resultant solid was dissolved in methylene dichloride (1200 mL), triethylamine (50 g, 0.495 mol) was added and heated to reflux. A solution of p-nitrobenzenesulfonyl chloride (93.0 g, 0.42 mol) in methylene chloride (300 mL) was added slowly to the reaction mixture at reflux temperature. After reaction complies by HPLC, water (500 mL) was charged to the reaction mixture. The two layers were separated and methylene dichloride was distilled under atmospheric pressure. Finally, methylene dichloride traces were removed by co-distillation with isopropyl alcohol. Isopropyl alcohol (1000 mL) was added to the mass, heated to reflux and maintained for 60 min. The reaction mass was cooled to 30-35° C., filtered and washed with isopropyl alcohol. The product obtained was dried at 70-75° C. to get the compound of formula 3a in 184 g (yield −92.88%) with HPLC purity of 99.26%.

Method B

A mixture of [N-(t-butoxycarbonyl)L-phenylalanine]chlorohydrine (6, 114 g, 0.38 mol), isobutylamine (28.5, 0.39 mol) and a solution of sodium bicarbonate (33.6 g, 0.4 mol in 100 mL) in methylene chloride (500 mL g) is heated at a gentle reflux for 5 h. Water (1000 g) is added and excess isobutyl amine is removed by distillation under nitrogen at an internal reaction temperature of 70° C. Additional water (500 g) is added and the product is isolated by filtration and dried. Finally, Isobutylamine traces were removed by flushing with methylene dichloride to get compound of formula 7. The resultant compound of formula 7 was dissolved in methylene dichloride (1200 mL), triethylamine (50 g, 0.495 mol) was added and heated to reflux. A solution of p-nitrobenzenesulfonyl chloride (93.0 g, 0.42 mol) in methylene chloride (300 mL) was added slowly to the reaction mixture at reflux temperature. After reaction complies by HPLC, water (500 mL) was charged to the reaction mixture. The two layers were separated and methylene dichloride was distilled under atmospheric pressure. Finally, methylene dichloride traces were removed by co-distillation with isopropyl alcohol. Isopropyl alcohol (1000 mL) was added to the mass, heated to reflux and maintained for 60 min. The reaction mass was cooled to 30-35° C., filtered and washed with isopropyl alcohol. The product obtained was dried at 70-75° C. to get the compound of formula 3a in 188 g with HPLC purity of 99.3%.

Example-2

Preparation of 4-amino-N-(2R,3S)(3-amino-2-hydroxy-4-phenylbutyl)-N-isobutylbenzenesulfonamide (4)

The compound of formula 3a (100 g), 10% palladium carbon (10 g) and triethanolamine (2 g) were suspended in methanol and then hydrogenated at 40-45° C. for 2 h. After completion of the reaction (TLC monitoring), filtered the reaction mass to remove palladium carbon. cp. HCl (62 mL) was added to the filtrate, heated to reflux and maintained for 2 h. The reaction mass was cooled to ambient temperature, pH of the reaction mass was adjusted to 6.0-7.0 with 20% sodium hydroxide solution. Methanol was distilled off under vacuum at below 50° C. The resultant residue was dissolved in a mixture of isopropyl alcohol (300 mL) and purified water (600 mL) and pH was further adjusted to 9.0-10.0 with 20% sodium hydroxide solution at ambient temperature. The reaction mass was maintained for 10 h, cooled to 0-5° C., filtered and washed with purified water. The wet cake was suspended in isopropyl alcohol (350 mL), heated to reflux, and maintained for 30 min. The reaction mass was cooled to 2-4° C., maintained for 1 h., filtered and washed with isopropyl alcohol. The wet product was air dried to obtain the compound of formula 4 in 71.3 g (yield-95%) with HPLC purity of 99.76%.

Example-3

Preparation of Durumvir Ethanolate

A solution of (3R,3aS,6aR)-hexahydrofuro[2,3-t]furan-3-yl 4-nitrophenyl carbonate (5b, 75.4 g) in N-methyl-2-pyrrolidinone (300 mL) was added to a pre-cooled (−2±2° C.) solution of the compound of formula 4 (100 g) in N-methyl-2-pyrrolidinone (200 mL) at −4 to 0° C. over a period of 2 h. The temperature of the reaction mass was slowly raised to 25-30° C. and maintained for 8 h. After completion of the reaction (TLC monitoring), ethyl acetate (1000 mL) and purified water (500 mL) were added to the reaction mass. The layers were separated; organic layer was washed with sodium carbonate solution (2×500 mL) followed by sodium chloride solution. The organic layer was concentrated; ethanol (300 mL) was added, heated to 45-50° C., maintained for 1 h, filtered and washed with ethanol. The wet compound was taken into a mixture of ethyl acetate-ethanol (7:93, 600 mL), heated to reflux, charcoal was added and filtered. The resultant filtrate was cooled to 0-5° C., filtered the separated solid and washed with ethanol. The wet compound was dried at 45° C. to obtain the in 124.3 g (yield-82.5%). The obtained Darunavir ethanolate had purity of 99.79% on area by HPLC and contained 0.08% on area by HPLC of the difuranyl impurity.

Preparation of Amorphous Darunavir

Example-4

A solution of Darunavir ethanolate (200 g) in dichloromethane (10 L) was taken into ATFD Feed tank. The solvent was evaporated by fed the solution slowly to the ATFD Vessel (feed rate 5 L/h) at 36-40° C. and high vacuum (580 mm/Hg) over 2 h and then flushed with dichloromethane (3 L). The material is collected in the material collector in 160 g with the HPLC Purity of 99.60% and particle size $D_{50}$ of approximately 50 micrometers and $D_{90}$ of approximately 100 to 180 micrometers.

Example-5

Darunavir Ethanolate (200 gm) was dissolved in Methylene chloride (1000 ml) and solvent was evaporated by applying vacuum followed by isolation of amorphous Darunavir as a solid as such or by charging n-Heptane or Isopropyl ether.

Example-6

Darunavir Ethanolate (10 g) was dissolved in ethyl acetate (50 mL). The solution was heated to 40-45° C. and maintained for 30 min. Ethyl acetate was distilled off under vacuum completely to get residue in the form of semisolid. n-Heptane (50 mL) was added to the residue and stirred for 30 min. at ambient temperature. The separated solid was filtered, washed the wet cake with n-Heptane (5 mL) and dried at 40-45° C. under vacuum to get 8.0 g of amorphous Darunavir.

Example-7

Darunavir Ethanolate (10 g) was placed into a dry round bottom flask and heated to 110-120° C. to melt and maintained under vacuum for 4 h. The reaction mass was slowly cooled to 25-35° C. The obtained glass type crystal was broken into powder to afford 8.5 g of amorphous Darunavir.

Example-8

Darunavir Ethanolate (5.0 g) was suspended into glycerol (25 g), heated to 110-120° C. under vacuum and maintained for 30 min. Water (50 mL) was added to the cooled reaction mass at 25-35° C. under stirring and the obtained suspension was stirred for 30 min at 25-35° C. The separated solid was filtered and dried at 40-45° C. under vacuum to yield 3.5 g of amorphous Darunavir.

Example-9

Carbonic acid [(1R,2S)-1-{((4-amino-benzenesulfonyl)-isobutyl-amino)-methyl}-2-((3R,3aS,6aR)-hexahydro-furo[2,3-b]furan-3-yloxycarbonylamino)-3-phenyl-propylester (3R,3aS,6aR)-hexahydro-furo[2,3-b]furan-3-yl ester (difuranyl impurity, 1).

The difuranyl impurity (1) isolated from the mother liquor by preparative HPLC using a mixture of formic acid-water (1:99) as eluent. The $^1$H-NMR, $^{13}$C-NMR and mass spectral data complies with proposed structure.

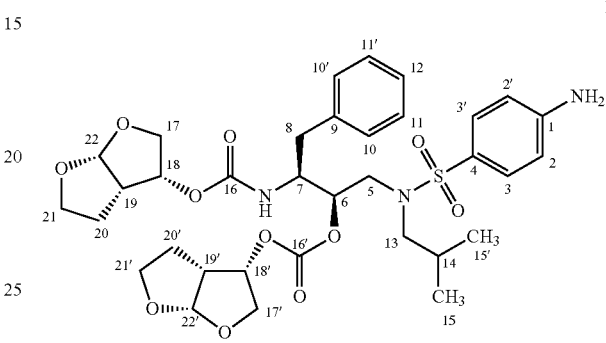

$^1$H-NMR (DMSO-d$_6$, 300 MHz, ppm)-δ 0.79 (d, J=6.6 Hz, 6H, 15 & 15'), 1.14-1.20 (m, 1H, 20Ha), 1.34-1.42 (m, 1H, 20Hb), 1.75-1.85 (m, 2H, 20'Ha & 14), 1.94-2.01 (m, 1H, 20'Hb), 2.54-2.64 (m, 2H, 8Ha & 13Ha), 2.74-2.89 (m, 3H, 8Hb, 13Hb & 19), 3.00-3.11 (m, 2H, 5Ha & 19'), 3.34-3.39 (m, 1H, 5Hb), 3.54-2.63 (m, 3H, 21Ha & 17Ha), 3.65-3.74 (m, 3H, 21'Ha, 21Hb &17Hb), 3.81-3.89 (m, 2H, 21'Hb & 17'Ha), 3.94-4.04 (m, 2H, 7 & 17'Hb), 4.81-4.88 (m, 1H, 6), 4.92-4.96 (m, 1H, 18'), 5.03-5.10 (m, 1H, 18), 5.11 (d, J=5.4 Hz, 1H, 22'), 5.61 (d, J=5.1 Hz, 1H, 22), 6.03 (brs, 2H, NH$_2$, D$_2$O exchangeable), 6.63 (d, J=8.7 Hz, 2H, 2 & 2'), 7.15-7.28 (m, 5H, 10H, 10'H, 11H, 11' & 12), 7.40 (d, J=8.7 Hz, 2H, 3 & 3'), 7.55 (d, J=9.3 Hz, 1H, NH, D$_2$O exchangeable).

$^{13}$H-NMR (DMSO-d$_6$, 75 MHz, ppm)-δ 19.56 & 19.81 (15C & 15'C), 25.42 (20'C), 25.47 (20C), 26.28 (14C), 35.14 (8C), 44.45 (19'C), 45.01 (19C), 49.21 (5C), 53.39 (7C), 57.55 (13C), 68.70 (21'C), 68.74 (21C), 69.95 (17'C), 70.20 (17C), 72.65 (6C), 76.27 (18C), 79.59 (18'C), 108.70 (22'C), 108.75 (22C), 112.69 (2C), 122.56 (4C), 126.12 (12C), 128.04 (11C & 11'C), 129.03 (10C & 10'C), 129.08 (3C), 138.03 (9C), 152.99 (1C), 153.55 (16'C), 155.32 (16C).

DIP MS: m/z (%) 1108 [M+H]$^+$, 1131 [M+Na]$^+$

Example-10

Unit Composition:

| S. No. | Ingredients | mg/tablet | % w/w |
|---|---|---|---|
| 1 | Darunavir | 600.00 | 46.15 |
| 2 | Microcrystalline cellulose | 630.00 | 48.46 |
| 3 | Crospovidone | 50.00 | 3.85 |
| 4 | Colloidal silicon dioxide | 10.00 | 0.77 |
| 5 | Magnesium stearate | 10.00 | 0.77 |
|  | Tablet weight | 1300.00 | 100.00 |
| 6 | Opadry ™ | 30.00 | — |

Brief Manufacturing Process:
a. Direct Compression:
1. Sift Darunavir, Microcrystalline cellulose, Crospovidone, Colloidal silicone dioxide and blend in blender
2. Sift Magnesium stearate and blend adding to Step 1
3. Compress the step 2 blend to tablets
4. Coat the core tablets using Opadry.
b. Roller Compaction:
1. Compact Darunavir and Microcrystalline cellulose using Roller compactor
2. Mill the compacts using suitable screen to get granules
3. Sift Crospovidone and Colloidal silicone dioxide and blend along with Step 2 granules.
4. Sift Magnesium stearate and blend adding to Step 3
5. Compress the step 4 blend to tablets
6. Coat the core tablets using Opadry.

Example-11

Unit Composition:

| S. No. | Ingredients | mg/tablet | % w/w |
|---|---|---|---|
| 1 | Darunavir | 600.00 | 46.15 |
| 2 | Microcrystalline cellulose | 580.00 | 44.61 |
| 3 | Crospovidone | 50.00 | 3.85 |
| 4 | Polyvinyl pyrrolidone | 50.00 | 3.85 |
| 5 | IPA: Water | Qs | Qs |
| 5 | Colloidal silicon dioxide | 10.00 | 0.77 |
| 6 | Magnesium stearate | 10.00 | 0.77 |
|  | Tablet weight | 1300.00 | 100.00 |
| 7 | Opadry ™ | 30.00 | — |

Brief Manufacturing Process:
1. Sift and mix Darunavir and Microcrystalline cellulose
2. Prepare PVP solution by stirring IPA/water and PVP
3. Granulate Step 1 ingredients using PVP solution
4. Dry the granules and mill to get granules
5. Sift Crospovidone and Colloidal silicone dioxide and blend along with Step 4 granules.
6. Sift Magnesium stearate and blend adding to Step 5
7. Compress the step 4 blend to tablets
8. Coat the core tablets using Opadry.

Example-12

Unit Composition:

| S. No. | Ingredients | mg/tablet | % w/w |
|---|---|---|---|
|  | Intra Granular |  |  |
| 1 | Darunavir | 600.00 | 50.42 |
| 2 | Microcrystalline cellulose | 135.00 | 11.34 |
| 3 | Crospovidone | 55.00 | 4.62 |
| 4 | Sodium starch glycolate | 65.00 | 5.46 |
| 5 | Colloidal silicon dioxide | 40.00 | 3.36 |
| 6 | Hypromellose | 25.00 | 2.10 |
| 7 | Water | Qs | Qs |
|  | Extra Granular |  |  |
| 8 | Microcrystalline cellulose | 125.00 | 10.50 |
| 9 | Crospovidone | 45.00 | 3.78 |
| 10 | Sodium starch glycolate | 65.00 | 5.46 |
| 11 | Colloidal silicon dioxide | 20.00 | 1.68 |
| 12 | Magnesium stearate | 15.00 | 1.26 |
|  | Tablet weight | 1190.00 | 100.00 |
| 13 | Opadry ™ | 30.00 | — |

Brief Manufacturing Process:
1. Sift and mix Darunavir, Microcrystalline cellulose, Crospovidone, Sodium Starch glycolate and Colloidal silicondioxide (intra granular part).
2. Prepare Hypromellose solution by dissolving in water using stirrer.
3. Granulate Step 1 ingredients using Hypromellose solution
4. Dry the granules and mill to get granules
5. Sift microcrystalline cellulose, Crospovidone, Sodium Starch glycolate and Colloidal silicon dioxide (extra granular part) and blend along with Step 4 granules.
6. Sift Magnesium stearate and add to Step 5 blend and mix it.
7. Compress the step 6 blend to tablets.
8. Coat the core tablets using Opadry.

The invention claimed is:
1. A process for the preparation of amorphous Darunavir containing less than 0.1% of the difuranyl impurity, comprising coupling the compound of formula 4 with (3R,3aS,6aR) hexahydrofuro [2,3-b]furan-3-ol derivative (5) in N-methyl-2-pyrrolidinone (NMPO)

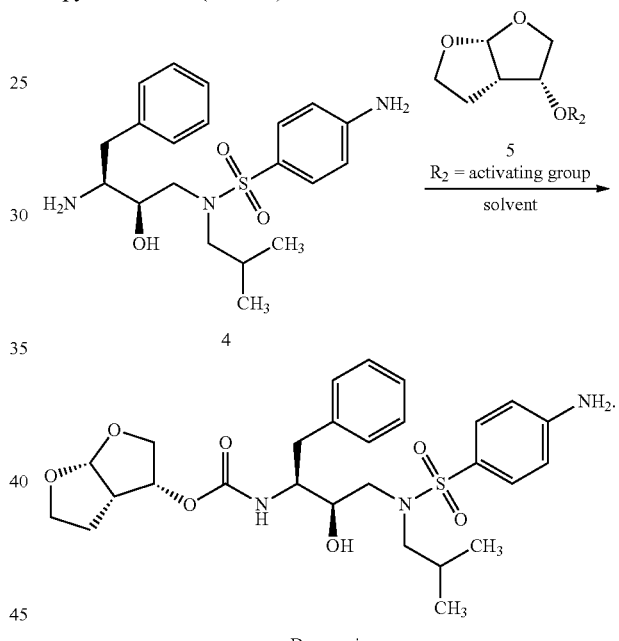

Darunavir

2. A process for the preparation of amorphous Darunavir containing less than 0.1% of the difuranyl impurity comprising the steps of:
a) coupling the compound of formula 4 with (3R,3aS,6aR) hexahydrofuro[2,3-b]furan-3-ol derivative (5) in N-methyl-2-pyrrolidinone (NMPO) to obtain Darunavir,

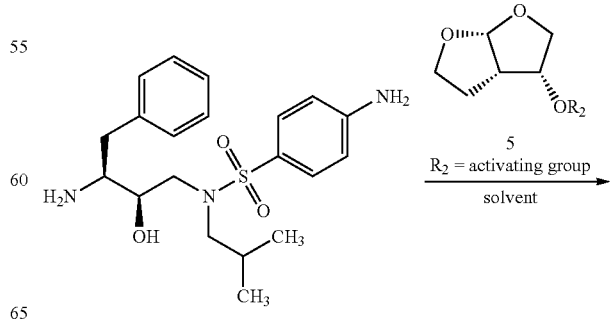

4

23
-continued

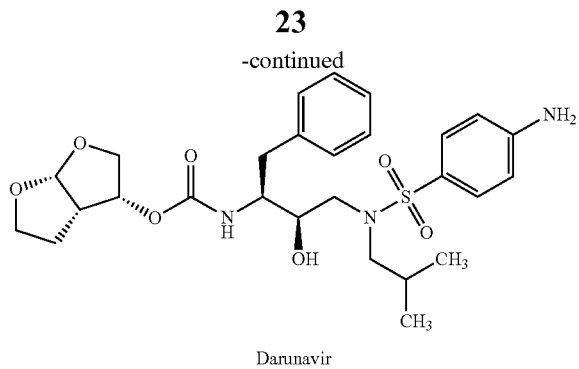

Darunavir b) optionally converting the Darunavir to Darunavir alcohol solvate,

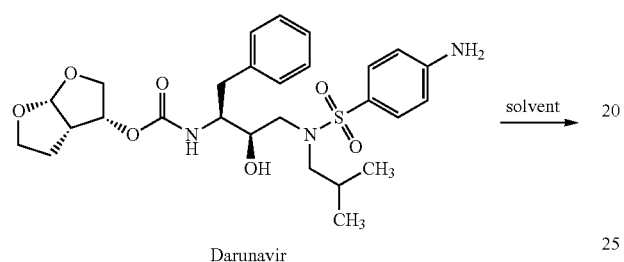

Darunavir

24
-continued

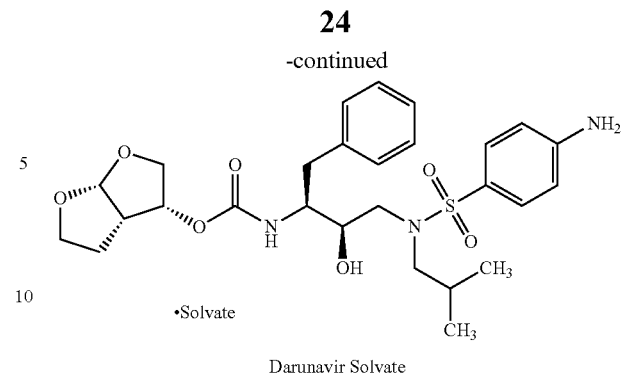

Darunavir Solvate c) dissolving the Darunavir or Darunavir alcohol solvate in a chlorinated organic solvent, and d) isolating amorphous Darunavir by agitated thin film drying (ATFD).

3. The process according to claim 2, wherein at least one of the solvents used in step c) is selected from the group consisting of dichloromethane, chloroform, dichloroethane, and mixtures thereof.

* * * * *